(12) United States Patent
Ji

(10) Patent No.: US 10,271,925 B2
(45) Date of Patent: Apr. 30, 2019

(54) ADJUSTABLE BRACKET, ORTHODONTICS SYSTEM WITH THE BRACKET AND TEETH ORTHODONTIC METHOD

(71) Applicant: Li Ji, Guangzhou (CN)

(72) Inventor: Li Ji, Guangzhou (CN)

( * ) Notice: Subject to any disclaimer, the term of this patent is extended or adjusted under 35 U.S.C. 154(b) by 44 days.

(21) Appl. No.: 14/983,193

(22) Filed: Dec. 29, 2015

(65) Prior Publication Data

US 2016/0128804 A1  May 12, 2016

Related U.S. Application Data

(63) Continuation of application No. PCT/CN2014/086850, filed on Sep. 18, 2014.

(30) Foreign Application Priority Data

Aug. 22, 2014 (CN) .......................... 2014 1 0418168

(51) Int. Cl.
*A61C 7/14* (2006.01)
*A61C 7/12* (2006.01)
(Continued)

(52) U.S. Cl.
CPC ............. *A61C 7/141* (2013.01); *A61C 7/12* (2013.01); *A61C 7/14* (2013.01); *A61C 7/20* (2013.01);
(Continued)

(58) Field of Classification Search
CPC .... A61C 7/12; A61C 7/14; A61C 7/20; A61C 7/22; A61C 7/28; A61C 7/287;
(Continued)

(56) References Cited

U.S. PATENT DOCUMENTS 3,721,005 A * 3/1973 Cohen ...................... A61C 7/14
                                                       433/16
4,139,945 A * 2/1979 DiGiulio .................. A61C 7/12
                                                       433/16
(Continued)

FOREIGN PATENT DOCUMENTS

CN          101662995         3/2010
CN          203710154         7/2014
(Continued)

OTHER PUBLICATIONS

International Search Report for application No. PCT/CN2014/086850, dated May 25, 2015 (4 pages).

*Primary Examiner* — Yogesh P Patel
(74) *Attorney, Agent, or Firm* — Hamre, Schumann, Mueller & Larson, P.C.

(57) ABSTRACT

An adjustable bracket is disclosed, including a main body and rotor, wherein the main body includes a base body which is provided with a base groove; the rotor is provided with a rotor body and a cover, the top of the rotor body is provided with a bracket slot, the cover is adapted to cover the top of the rotor body and cover the top of the opening of the bracket slot, the rotor is adapted to be pivotably connected to the base body, and the base body is further provided with a positioning portion for securing the rotor. An orthodontics system with the bracket and an orthodontic method are also disclosed. The adjustable bracket according to the present disclosure can be adjustable in torque, tip and the direction of the torsion on the tooth, and it can achieve a good corrective effect by simple operation.

13 Claims, 19 Drawing Sheets

(51) Int. Cl.
*A61C 7/28* (2006.01)
*A61C 7/20* (2006.01)
*A61C 7/22* (2006.01)

(52) U.S. Cl.
CPC .................. *A61C 7/22* (2013.01); *A61C 7/28* (2013.01); *A61C 7/287* (2013.01)

(58) Field of Classification Search
CPC ....... A61C 7/34; A61C 7/141; A61C 11/0604; A61C 11/106
USPC .......................... 433/8–16; 403/122–144, 90
See application file for complete search history.

(56) References Cited

U.S. PATENT DOCUMENTS

| | | | | |
|---|---|---|---|---|
| 4,171,568 A | * | 10/1979 | Forster | A61C 7/02 433/10 |
| 4,655,708 A | * | 4/1987 | Fujita | A61C 7/285 433/10 |
| 5,302,121 A | * | 4/1994 | Gagin | A61C 7/12 433/10 |
| 5,813,852 A | | 9/1998 | Kawaguchi | |
| 6,328,269 B1 | * | 12/2001 | Krautloher | F16C 11/0614 248/288.11 |
| 6,382,969 B1 | * | 5/2002 | Elnajjar | A61C 11/02 433/60 |
| 2004/0229184 A1 | * | 11/2004 | Senini | A61C 7/28 433/10 |
| 2006/0069389 A1 | | 3/2006 | Knopfle | |
| 2007/0259304 A1 | | 11/2007 | Hagelganz et al. | |
| 2010/0311004 A1 | * | 12/2010 | Voudouris | A61C 7/14 433/11 |
| 2013/0330683 A1 | * | 12/2013 | Wang | A61C 7/287 433/11 |
| 2014/0045134 A1 | * | 2/2014 | Hantusch | B23K 23/00 432/227 |
| 2014/0045137 A1 | | 2/2014 | Solano Reina et al. | |
| 2014/0141383 A1 | * | 5/2014 | Hagelganz | A61C 7/287 433/9 |
| 2014/0205962 A1 | * | 7/2014 | Damon | A61C 7/14 433/13 |
| 2014/0272751 A1 | * | 9/2014 | Cosse | A61C 7/02 433/9 |
| 2015/0017597 A1 | * | 1/2015 | Solano Reina | A61C 7/14 433/10 |
| 2015/0157422 A1 | * | 6/2015 | Cosse | A61C 7/14 433/16 |
| 2015/0305833 A1 | * | 10/2015 | Cosse | A61C 7/002 433/3 |

FOREIGN PATENT DOCUMENTS

| | | |
|---|---|---|
| CN | 204207867 | 3/2015 |
| EP | 0727192 | 8/1996 |
| JP | 3621737 | 2/2005 |
| WO | 9400072 | 1/1994 |

* cited by examiner

220

ADJUSTABLE BRACKET, ORTHODONTICS SYSTEM WITH THE BRACKET AND TEETH ORTHODONTIC METHOD

FIELD

The present disclosure relates generally to a fix-orthodontic technique and the field of orthodontics, and more particularly, to an adjustable bracket, an orthodontics system with the bracket and an orthodontic method.

BACKGROUND

As an important unit in the fix-orthodontic technique, a bracket is an orthodontic appliance for correcting deformity of the teeth. The bracket can be bonded directly to the surface of dental crowns, and various types of orthodontic forces can be applied to the tooth by an arch wire via the bracket, so as to realize orthodontic treatment.

At present, the tie wings, bracket slot and bracket base included in the bracket around the world are all integrated as one, the arch wire used for orthodontic treatment is fixed inside the bracket slot, and the tooth and the bracket may slide as a whole along the arch wire. A certain angle is formed between the bracket slot and the bottom of bracket, this angle and the inclination can determine the labial-lingual (labial-palatal) inclination (torque) of teeth, the axis inclination (tip) at a mesial direction and a distal direction, and the rotation of tooth body. There are many standards about the angle and the inclination of the bracket slot around the world, however, each type of data has its advantages and disadvantages, thus argument about qualities of each data never stops. All bracket slots of traditional brackets are fixed at present, and for a set of brackets, different brands or producers may use different data of the bracket slot. Orthodontists are faced with various patients requiring orthodontic treatment, so a bracket with one type of data may be hard to meet the requirement of orthodontic treatment.

SUMMARY

In view of the above problems, it is an object of the present disclosure to provide an adjustable bracket, in which the torque, tip and the direction of the torsion on the tooth can be adjusted while a good corrective effect can be achieved by simple operation.

According to an aspect of the present disclosure, an adjustable bracket is provided, including:

a main body including a base body which is provided with a base groove;

a rotor, provided with a rotor body and a cover, wherein the top of the rotor body is provided with a bracket slot, the cover is adapted to cover the top of the rotor body and cover the top of a slot opening of the bracket slot, the rotor body is adapted to be pivotably connected to the base body, and the base body is further provided with a positioning portion for securing the rotor.

In the adjustable bracket related according to the present disclosure, the rotor can be moved at any angle through the cooperating between the main body and the rotor. After every adjustable bracket is fixed on the surface of the teeth through the respective base body, because the arrangement of the teeth may be irregular, and the arch wire for fixation may not completely match all the adjustable brackets, the rotor can be moved at a certain angle following the line route of the arch wire so that the position of the bracket slot can be adjusted to match the line route of the arch wire.

According to the present disclosure, the bracket can be divided into two parts (a main body and a rotor) or made up of more small components. The main principle of the present disclosure is to separate the part with the bracket slot from the main body of the bracket, to adjust the parameter of the bracket slot by turning the portion with the bracket slot or changing the position of the bracket slot.

In one embodiment, the base groove has an inner wall shaped as a smooth curved surface; and the rotor has a smooth curved surface so that the rotor is in a shape similar to a sphere, and the rotor is disposed within the base groove and pivotably fit with the base groove In the adjustable bracket related according to the present disclosure, the rotor can be moved at any angle within the base groove through the cooperating between the base groove with a smooth curved surface provided in the main body and the rotor with a smooth curved surface. After every adjustable bracket is fixed on the surface of the teeth through respective base body, because the arrangement of the teeth may be irregular, and the arch wire for fixation may not completely match all the adjustable brackets, the rotor can be moved at a certain angle following the line route of the arch wire so that the position of the bracket slot can be adjusted to match the line route of the arch wire.

In one embodiment, the base groove has an inner wall shaped as a smooth spherical surface; and the rotor body has a smooth spherical surface, and the cover has a spherical surface that matches the surface of the rotor body. The design of the spherical surface can facilitate the matching between the rotor and the base groove, so the rotor can be moved within the base groove more flexibly and freely, resulting in a large moving range.

In one embodiment, two sides of the rotor body respectively located at two ends of a transverse opening of the bracket slot are in a flat shape so that the rotor body is in a shape of spherical segment; and the thickness of the rotor body in a direction along the transverse opening of the bracket slot is less than the minimum width of the base groove in a direction perpendicular to the transverse opening of the bracket slot. The rotor body is designed to be in a shape of spherical segment, and the thickness of the rotor body in a direction along the transverse opening of the bracket slot is designed to be less than the minimum width of the base groove, so it can facilitate to put the rotor in the base groove when the base body is designed as one-piece, and also facilitate to take the rotor out of the base groove. The thickness of the rotor body in a direction along the transverse opening of the bracket slot is less than the minimum width of the base groove in a direction perpendicular to the transverse opening of the bracket slot, so the rotor is easy to be put in the base groove. After the rotor has been put in the base groove, the rotor can be turned 90 degrees horizontally within the base groove that the rotor will not fall out of the base groove, and at this moment, the opening of the bracket slot is in the same direction as the opening of the base groove, so it can facilitate the placement of the arch wire. For taking the rotor out of the base groove, it normally requires turning the rotor horizontally 90 degrees that the rotor is removable.

In one embodiment, two sides of the base body respectively located at two ends of a transverse opening of the base groove are in a flat shape. The surfaces of two sides of the base body are in flat shape so that it is easy to hold the portions of the rotor that are convex with respect to the two sides of the base body when fitting the rotor in the base groove or removing the rotor from the base groove, which immensely facilitates the fitting and removing of the rotor.

The surfaces of two sides of the base body are in flat shape so that the bracket slot of the rotor has a lager moving range within the base groove, that is, the bracket slot has a high mobility in the base groove. When the bracket slot of the rotor is turned to the right and left in horizontal direction, the bracket slot has a larger range of deflection angle. After the arch wire passing through the bracket slots, the bracket slots of the rotors on two teeth of different height can shift towards each other, and the arch wire has a gradually changed deformation, to avoid sharply bending of the arch wire.

In one embodiment, the bracket slot divides the rotor body into a first end portion and a second end portion, a first stopping groove is arranged at the top of the first end portion, and the first stopping groove is provided with a stopping opening located in the bracket slot;

a second stopping groove is arranged at the top of the second end portion, and the second stopping groove are provided with two sliding openings located in the same axis as the stopping opening of first stopping groove; and the cover is adapted to be held in the first and second stopping grooves, and cover the top of the slot opening of the bracket slot.

A recess can be formed between the first stopping groove and the second stopping groove, which facilitates to cover the bracket slot together with the cover, to avoid the arch wire being slipped off.

In one embodiment, each of the first stopping groove and the second stopping groove comprises two inward flanging edges with a round smooth shape; and the cover comprises top edges corresponding to the groove wall of the first stopping groove and the groove wall of the second stopping groove, configured to be concave to form two sliding grooves matching the inward flanging edges. A stopping structure is further formed by the inward flanging edges of the first stopping groove, the inward flanging edges of the second stopping groove and the sliding grooves of the cover. When the cover is slipped into the rotor body, the inward flanging edges can avoid the deviation from the longitudinal movement of the cover, and prevent the cover from falling off during use.

In one embodiment, the bottom of the second stopping groove is provided with a first bulge, the bottom of the cover is provided with a first groove of an elongated shape, and the long axis of the first groove is perpendicular to a line joining two lateral openings of the base groove. The first bulge arranged on the bottom of the second stopping groove can match the first groove of the elongated shape on the bottom of the cover to avoid falling off caused by excess sliding. When the cover is required to be removed, the cover always bears too much force due to uneven forces, and the cover may be taken out of the rotor body quickly, resulting in a local damage within the mouth cavity. The first bulge matching the first groove of the elongated shape can avoid applying too much force on the cover caused by uneven forces, and prevent the cover from being taken out of the rotor body quickly.

The first bulge has a larger size at the top of the first bulge than at the bottom of the first bulge, the first groove has a smaller size at the slot opening of the first groove than at the inside of the first groove, and the slot opening of the first groove is provided with a window matching the top end of the first bulge and adapted to be inserted by the top end of the first bulge The first bulge has a larger size at the top of the first bulge than at the bottom of the first bulge, so a structure of big top and small bottom can be formed to secure the first groove of the cover to avoid deviation from the longitudinal movement of the cover, and prevent the cover from slipping off.

In one embodiment, the base body is provided with a thread through hole to form the positioning portion, one end of the thread through hole is opened at the inner wall of the base groove, the other end of the thread through hole is opened at the surface of the main body, and the thread through hole is fitted with a retaining screw through which the rotor is fixedly connected to the main body. The thread through hole is designed to insert the retaining screw for retaining the positioned rotor, so that the turning angle and direction of the rotor are fixed, and the rotor is not easy to have a transitional movement.

In one embodiment, an end of the retaining screw towards the outside of the base body protruding 0.2 to 8 mm from the surface of the base body, and the end of the retaining screw is connected with a screw cap which protrudes radially and outwardly from the outer wall of the retaining screw.

In one embodiment, the main body further comprises a bottom plate comprising a top surface and a bottom surface, the base body is fitted on the top surface of the bottom plate, one side of the edge of the base body towards the top surface of the bottom plate is provided with a recess, and the recess and the bottom plate form a second groove; and at least two second grooves are formed, and all second grooves are distributed evenly on the side of the edge of the base body towards the top surface of the bottom plate. In this way, it is easy for the ligature wire to be tied with and fixed on the second groove, and the adjustable bracket can be further fixed to the arch wire by the effects of the ligature wire and the second groove, resulting in a better orthodontic effect.

In one embodiment, a guide groove is arranged on the top of the cover, which facilitates the angle adjustment of the rotor, and is easy to use.

In one embodiment, the first bulge is an elastic component

It is another object of the present disclosure to provide an orthodontics system with a bracket.

According to another aspect of the present disclosure, an orthodontics system with a bracket, includes an arch wire, and further includes an adjustable bracket, wherein the arch wire passes through the bracket slot of the adjustable bracket.

It is a further object of the present disclosure to provide an orthodontic method.

According to a further aspect of the present disclosure, an orthodontic method includes:

fixing a base body of a main body of an adjustable bracket on the surface of a tooth by adhesion;

passing an arch wire through a bracket slot of the adjustable bracket, covering a rotor with a cover, fixing the arch wire, and turning the rotor to allow a bottom plate of the main body of the adjustable bracket to match the arrangement and form of teeth, also allow a bracket slot of the rotor of the adjustable bracket to adapt the arrangement and form of the teeth, and further allow a channel of the bracket slot of the rotor of the adjustable bracket to adapt the position of the arch wire, wherein the arch wire generates a deformation force, a positioning portion of the base body positions the rotor, and a restoring force generated by the deformed arch wire is adapted to correct the teeth; and resetting the positioning portion once the orthodontic treatment has been performed for a predetermined time period, turning the corresponding rotor respectively again according to the arrangement and form of a part of the corrected teeth of patient, correcting and positioning the corresponding rotor to allow the channel of the bracket slot of the rotor to match the position of the arch wire, and also allow the expression of the angles of torque, tip and torsion presented in the bracket slot of the rotator to be adaptable to a corresponding facial type defined by alveolar bone and skull, and repeating the resetting, turning, correcting and positioning process to let the positioning portion on the base body position the rotor.

The orthodontic method according to the present disclosure has advantages of convenient operation, simple producing, low cost, easy manual operation, saving time and manpower, and safe in use.

The adjustable bracket according to the present disclosure can be free to adjust the torque depending on the way for the orthodontic treatment and targets to be achieved by the orthodontic treatment. In addition, it is not required to replace the bracket for adjusting the torque of the bracket in the orthodontic treatment.

In addition, "tip angle" is an angle of inclination of the long axis of the tooth with respect to the vertical centre line at a mesial direction and a distal direction, and may differ depending upon the race and the orthodontics system, as same as the torque angle of the bracket slot. The tip angle is adjustable that the angle of inclination of the tooth can be adjusted depending upon the doctor's experience. The inclination of the tooth is one of the most common dentofacial deformities, so the adjustable tip angle can slow down and reduce the force applied on the tooth to decrease the damage to the periodontium. Accurate adjustment can be also made for irregular teeth.

The turning angle of the tooth is adjustable. In the traditional brackets, there is no turning angle, so the dentist must glue the bracket on the center of tooth, but the tooth will be turned due to the crowding of teeth in many cases. Especially, the turning of the premolar is more common. Given this, the bracket may not be glued on the center of the tooth in many cases. However, for the bracket according to the present disclosure, the turning angle of the bracket is adjustable, so even if the bracket is not glued on the center of the tooth, the turning of the tooth can be corrected by adjusting the turning angle of the bracket.

The adjustable bracket according to the present disclosure can simplify the operation, and realize orthodontic treatment with light force. It can be adjusted in various angles without the need to replace the bracket. For a severe displaced tooth, each slight angle adjustment can achieve a good orthodontic effect with a very light orthodontic force, and the force applied on the periodontium and the root is very slight, so the health of the periodontium and the root can be protected.

DESCRIPTION OF REFERENCE NUMBERS

The reference numbers used herein includes: 10 main body, 110 base body, 112 base groove, 114 thread through hole, 116 recess, 118 second bulge, 120 bottom plate, 130 second groove, 140 retaining screw, 20 rotor, 210 rotor body, 211 bracket slot, 212 first end portion, 213 second end portion, 214 first stopping groove, 215 second stopping groove, 216 inward flanging edge, 217 first bulge, 220 cover, 221 protuberance, 222 guide groove, 223 first groove, and 224 first groove window.

DETAILED DESCRIPTION OF THE PREFERRED EMBODIMENTS

In the following description of embodiments, reference is made to the accompanying drawings which form a part hereof, and in which it is shown by way of illustrating specific embodiments of the disclosure that can be practiced. It is to be understood that other embodiments can be used and structural changes can be made without departing from the scope of the disclosed embodiments.

It will be understood that, when a feature or element is referred to as being "fixed" to another feature or element, it can be directly fixed to the other feature or element or intervening features or elements may be present. It will also be understood that, when a feature or element is referred to as being "connected", "attached" or "coupled" to another feature or element, it can be directly connected, attached or coupled to the other feature or element or intervening features or elements may be present.

Unless otherwise specified, all the terminology and scientific terms used herein have the same meaning as understood by those skilled in the art to which the present invention pertains. Terms used herein are for the purpose of describing particular embodiments only and are not intended to be limiting of the invention. For example, as used herein, the term "and/or" includes any and all combinations of one or more of the associated listed items.

Figure 24:
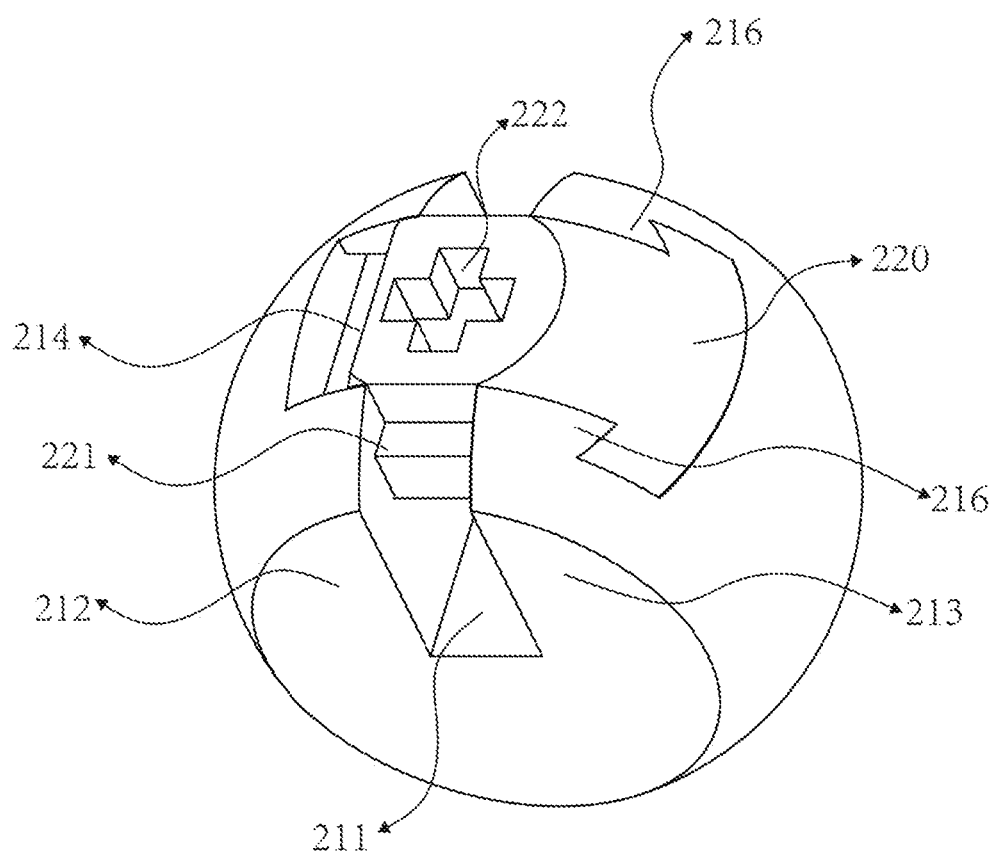
FIG. 24 is a plan view illustrating a rotor according to one embodiment of the present disclosure.

As shown in FIGS. 16-23, an adjustable bracket includes a main body 10 and a rotor (see FIG. 24). The main body 10 includes a base body 110 (see FIGS. 1-4), and the base body 110 has an overall shape similar to a rectangular solid. The top of the base body 110 is provided with a base groove 112 passing through the base body 110 along the short axis of the base body 110. The base groove 112 is open upwards at the top of the base body 110, and also open in transverse direction at the two lateral sides of the base body 110 as a transverse opening. The inner wall of the base groove 112 has an inner wall shaped as a smooth curved surface, preferably, a smooth spherical surface. The surfaces of two sides of the base body 110 respectively located at two ends of the transverse opening of the base groove 112 are in flat shape, and two sides of the base body 110 perpendicular to the transverse opening of the base groove 112 has a convex surface respectively, so the base body 110 has an overall shape similar to a rectangular solid.

The thickness of the base body 110 in a direction along the transverse opening of the base groove 112 is less than the maximum width of the base groove 112 in a direction perpendicular to the transverse opening. The minimum width of the base groove 112 in a direction perpendicular to the transverse opening of the base groove 112 is larger than the distance between the two side surfaces of rotor body 210 in a flat shape. This design facilitates to put the rotor body 210 in the base groove 112. When the rotor body 210 is to be put in the base groove 112, the two side surfaces of rotor body 210 in a flat shape should be aligned with the inner wall of the base groove, and at this moment, the bracket slot 211 of the rotor body is perpendicular to the transverse opening of the base groove 112. Because the minimum width of the base groove 112 in a direction perpendicular to the transverse opening of the base groove 112 is larger than the distance between the two side surfaces of rotor body 210 in a flat shape, the rotor body 210 can be put in the base groove 112 in the above direction. After the rotor body 210 being put in the base groove 112, the rotor body 210 may be turned 90 degrees horizontally, and at this moment, the two side surfaces of rotor body 210 in a flat shape are aligned with the lateral openings of the base groove 112, and the bracket slot 211 of the rotor body 210 is parallel to the transverse opening of the base groove 112, that is, the transverse opening of the bracket slot 211 of the rotor body 210 has an opening direction identical to the transverse opening of the base groove 112, which facilitates to introduce the arch wire and prevent the rotor body 210 from falling off the base groove 112.

Figure 1:
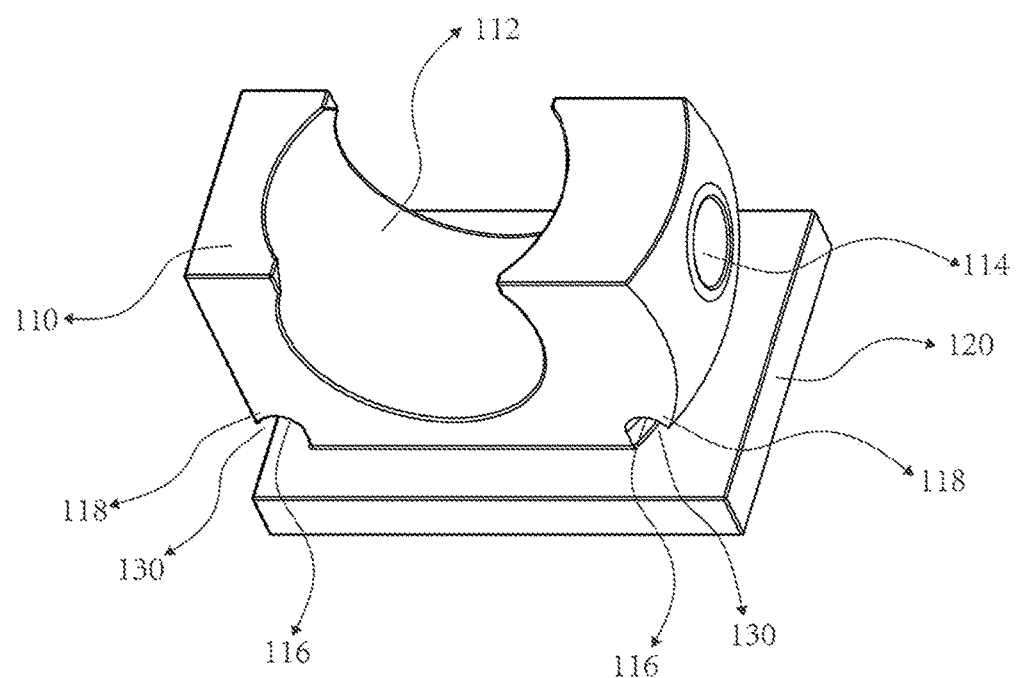
FIG. 1 is a plan view illustrating a main body according to one embodiment of the present disclosure.
Figure 2:
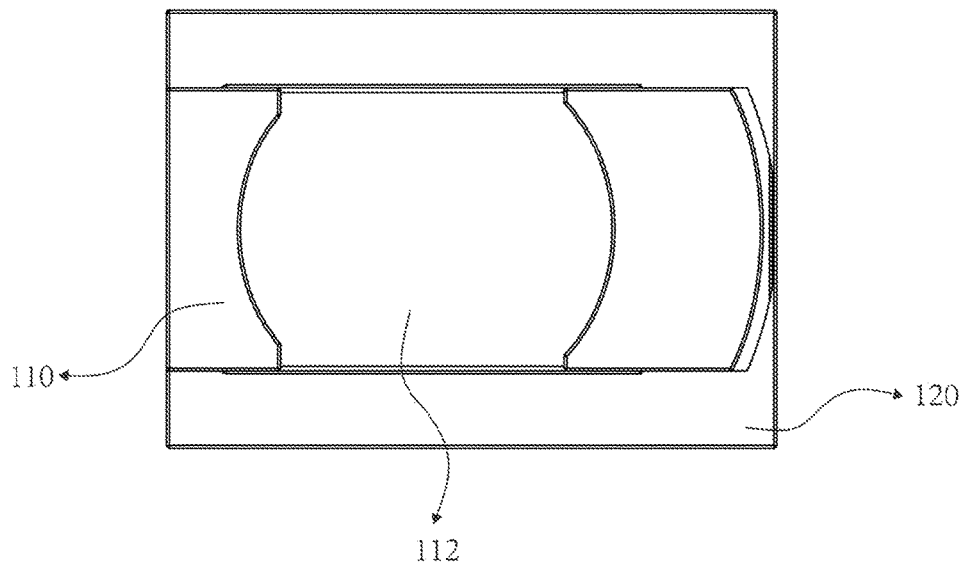
FIG. 2 is a top view illustrating a main body according to one embodiment of the present disclosure.
Figure 3:
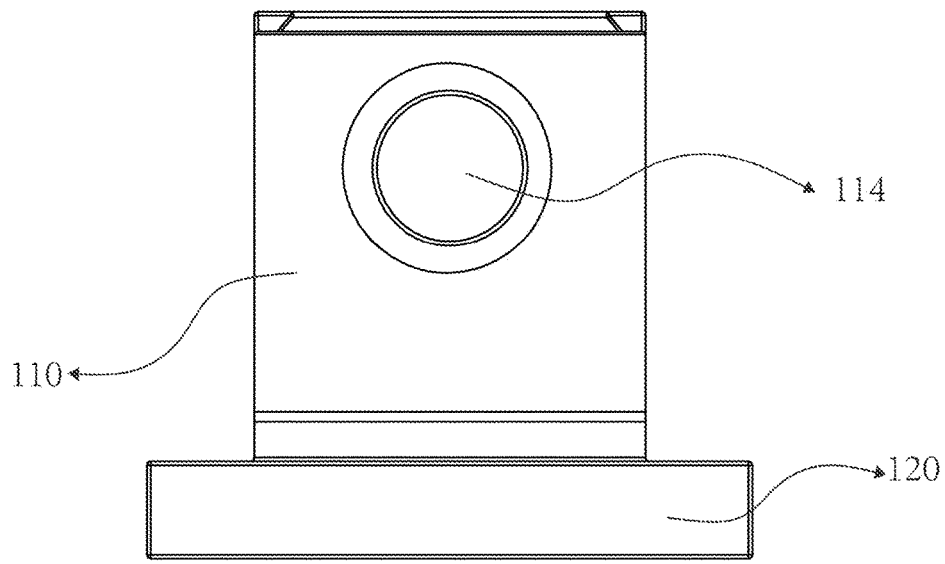
FIG. 3 is a right side view illustrating a main body according to one embodiment of the present disclosure.
Figure 4:
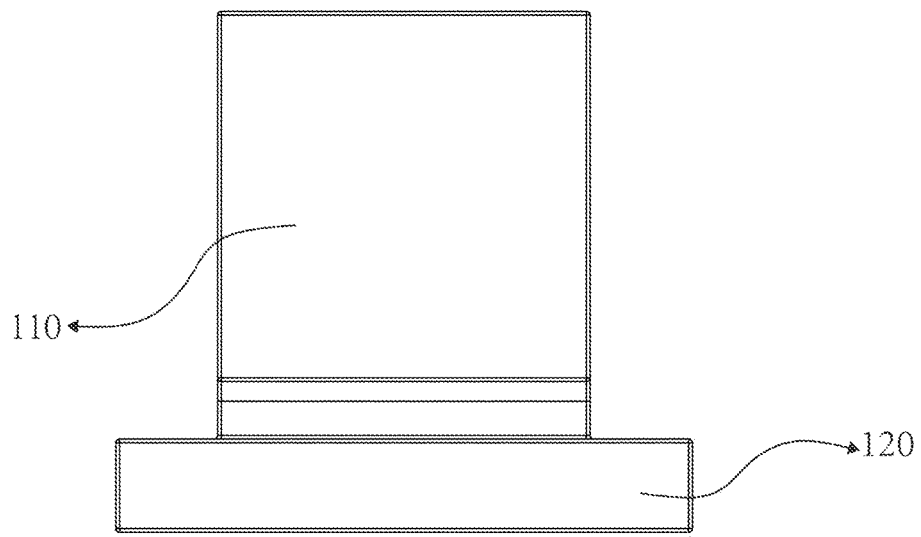
FIG. 4 is a left side view illustrating a main body according to one embodiment of the present disclosure.
Figure 5:
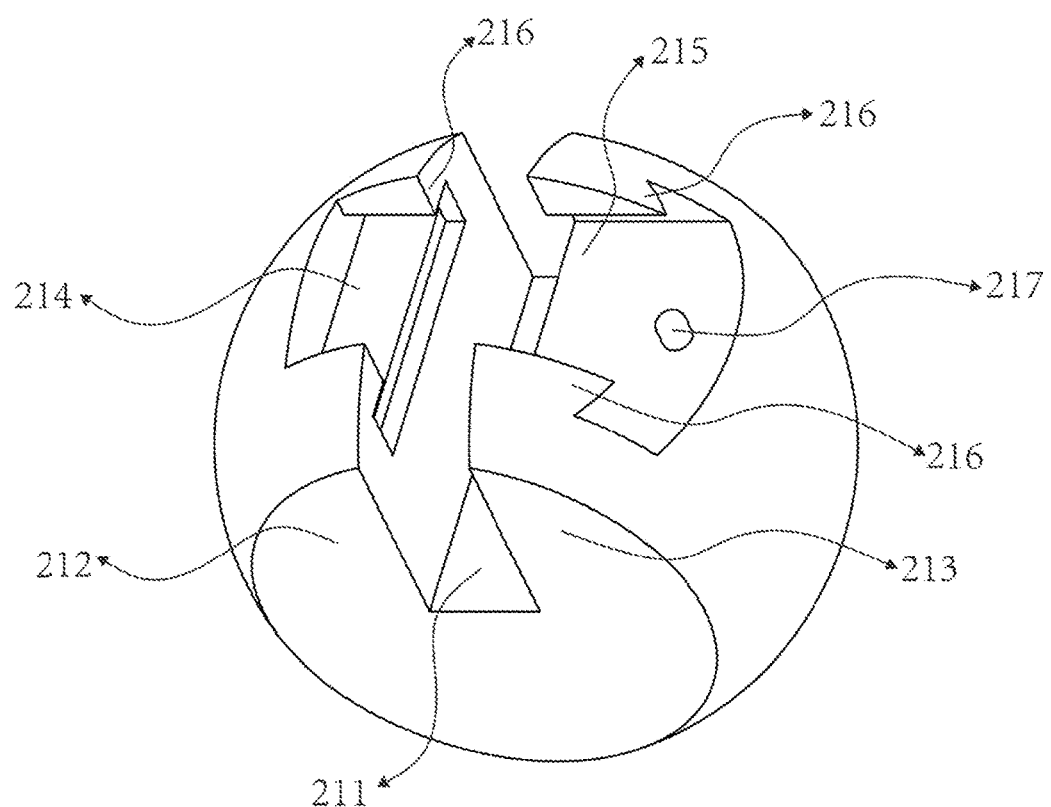
FIG. 5 is a plan view illustrating a rotor body according to one embodiment of the present disclosure.
Figure 6:
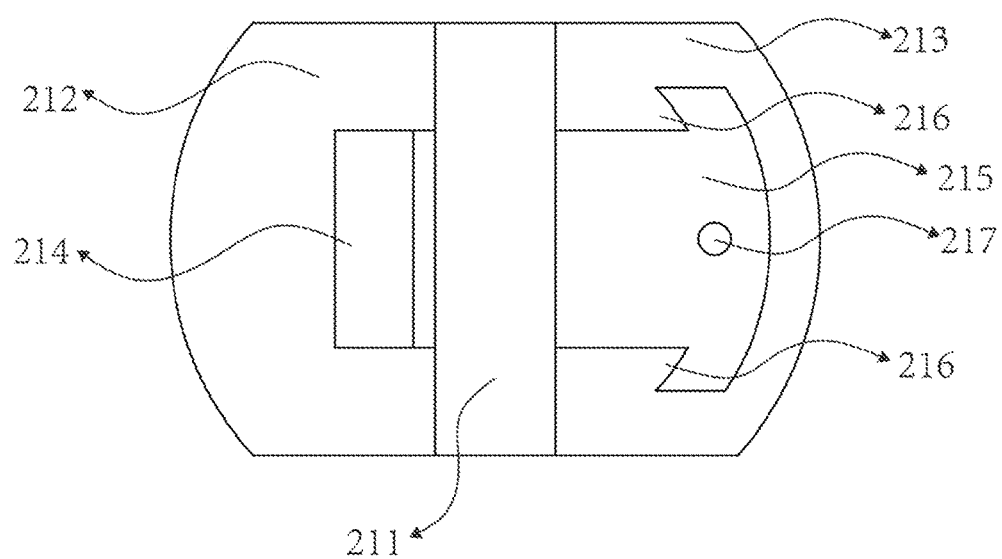
FIG. 6 is a top view illustrating a rotor body according to one embodiment of the present disclosure.
Figure 7:
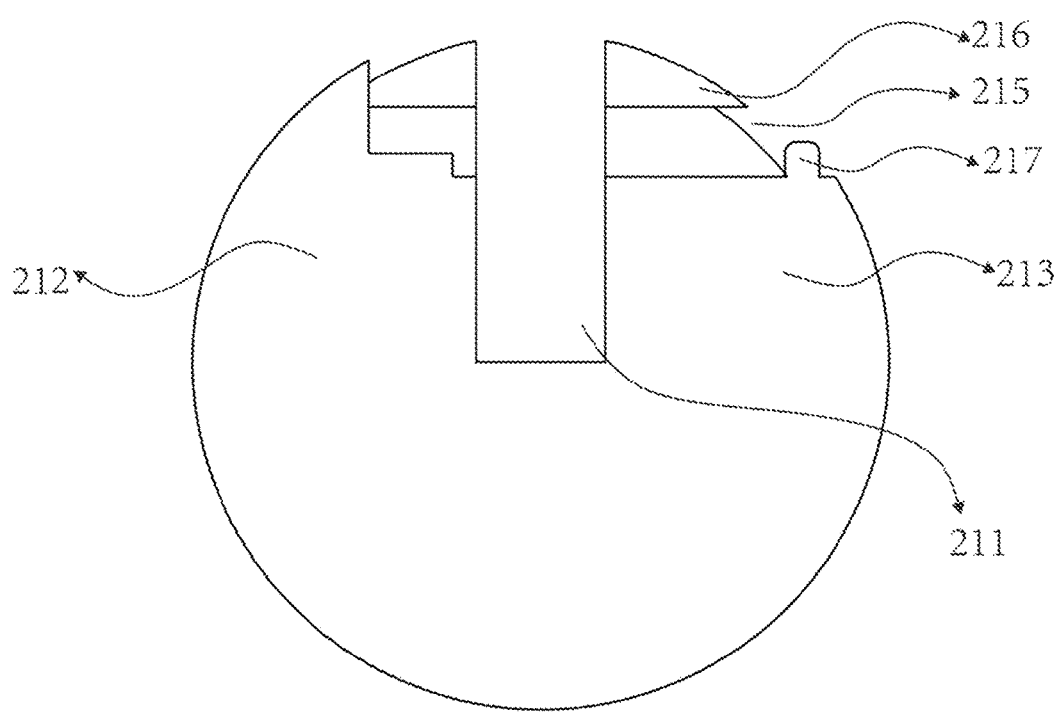
FIG. 7 is a front view illustrating a rotor body according to one embodiment of the present disclosure.
Figure 8:
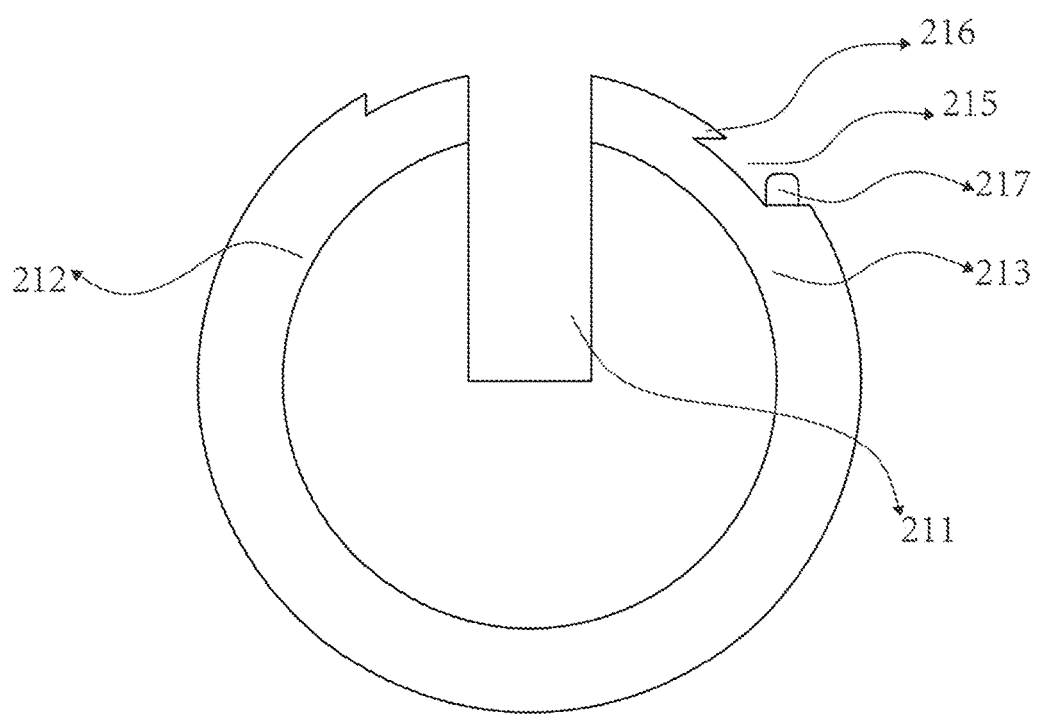
FIG. 8 is a back view illustrating a rotor body according to one embodiment of the present disclosure.

As shown in FIGS. 5, 8 and 24, the rotor 20 is provided with a rotor body 210 and a cover 220. The rotor body 210 has a smooth curved surface, preferably, a smooth spherical surface. The rotor 20 may be arranged within the base groove 112, and the rotor 20 may be clearance fitted in the base groove 112, that is, the rotor 20 may be freely moved within the base groove 112. The top of the rotor body 210 is provided with a bracket slot 211 configured to place the arch wire. The bracket slot 211 has a shape similar to a rectangular solid. The bracket slot 211 is open upwards at the top of the base body 110, and also open in transverse direction at the two lateral sides of the rotor body 210 as a transverse opening. The transverse opening of the bracket slot 211 of the rotor body 210 has an opening direction identical to the transverse opening of the base groove 112.

Figure 9:
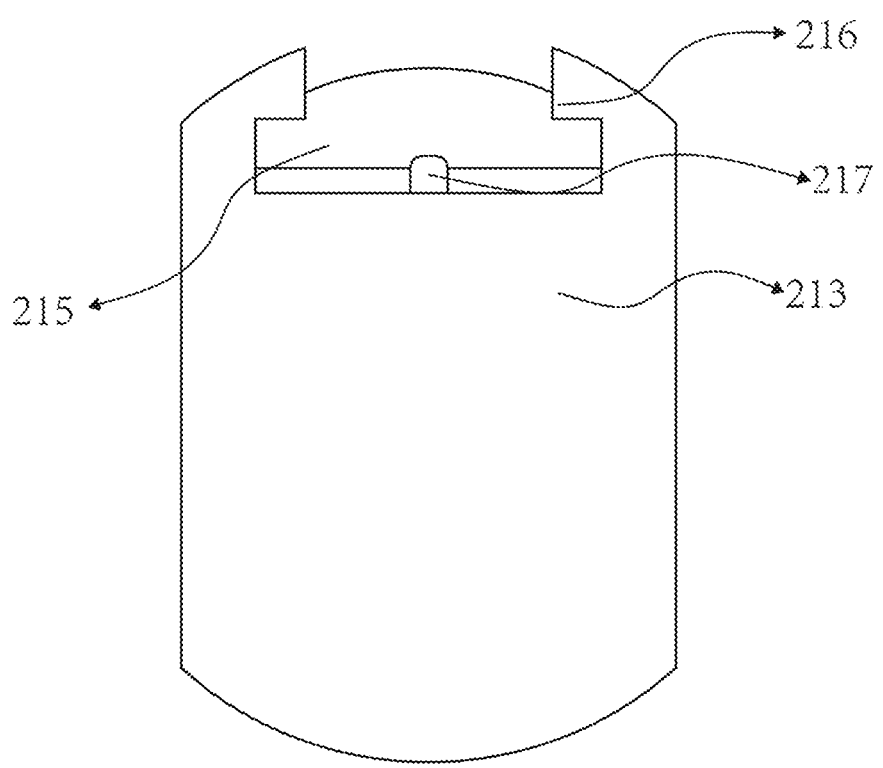
FIG. 9 is a right side view illustrating a rotor body according to one embodiment of the present disclosure.

As shown in FIG. 8, the bracket slot 211 divides the rotor body 210 into a first end portion 212 and a second end portion 213. As shown in FIG. 9, a first stopping groove 214 is arranged at the top of the first end portion 212, and the first stopping groove 214 is provided with two openings. One of the two openings is a top opening, which is open upwards at the top of the rotor body 210 and has an opening direction identical to the top opening of the bracket slot 211, and the other of the two openings is a lateral opening located in the bracket slot 211 and is open towards the second end portion 213.

Figure 10:
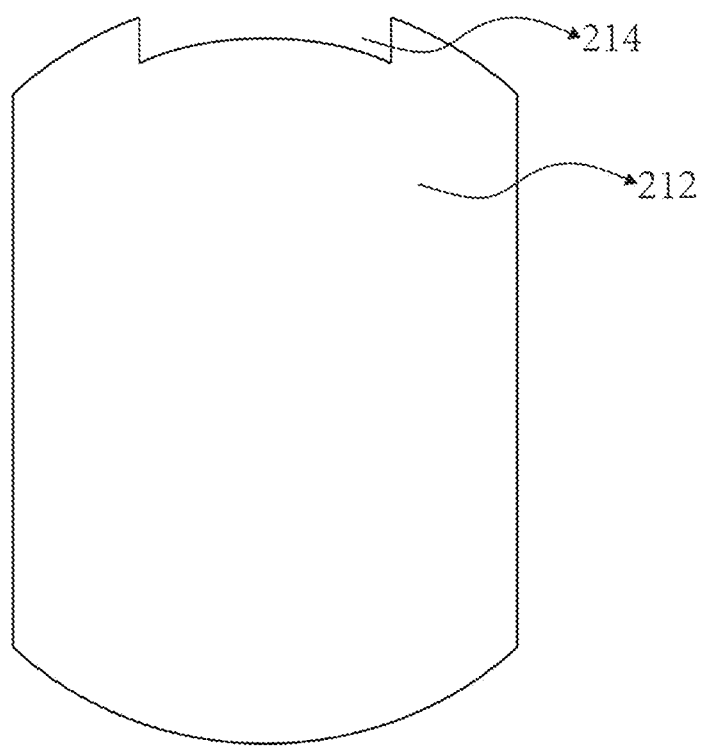
FIG. 10 is a left side view illustrating a rotor body according to one embodiment of the present disclosure.

As shown in FIG. 10, a second stopping groove 215 is arranged at the top of the second end portion 213. The second stopping groove 215 is provided with three openings. One of the three openings is a top opening, which is open upwards at the top of the rotor body 210 and has an opening direction identical to the top opening of the bracket slot 211. The other two of the three openings are lateral openings located at a same axis, one is open towards the first end portion 212, and the other is open outwards from the rotor body 210. The two sliding openings of the second stopping groove 215 and the stopping opening of the first stopping groove 214 are located at a same axis.

As shown in FIGS. 11, 12, 14 and 15, the cover 220 is adapted to be held in the first and second stopping grooves 214, 215, and cover the top of the slot opening of the bracket slot 211. The top of the cover 220 has a partially smooth curved surface, preferably, a partially spherical surface, which can match the surface of the rotor body 210 so that the rotor 10 is in a shape of a sphere.

Figure 11:
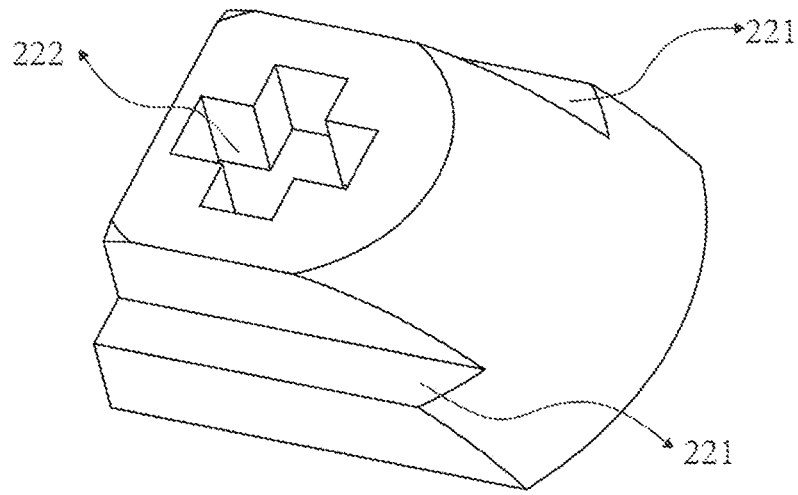
FIG. 11 is a plan view illustrating a cover according to one embodiment of the present disclosure.
Figure 12:
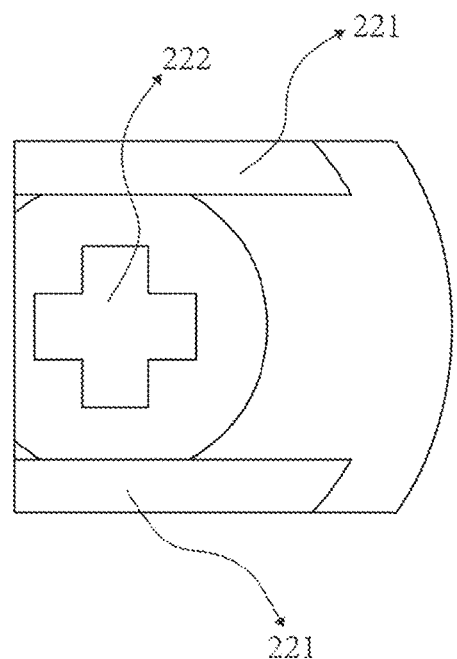
FIG. 12 is a top view illustrating a cover according to one embodiment of the present disclosure.

Further, as shown in FIG. 11, a guide groove 222 is arranged on the top of the cover 220. The guide groove 222 may be in a shape of cross, hexagon, pentagon or others general graphics. In the embodiment, the guide groove 222 is in a shape of cross. The guide groove facilitates to open the cover 220 and adjust the angle and direction of the rotor 20 within the base groove 112.

Further, two sides of the rotor body 210 respectively located at two ends of the transverse opening of the bracket slot 211 (in long axis direction) are in a flat shape so that the rotor body 210 is in a shape of spherical segment. The flat shape is formed by cutting a part of a sphere. The thickness between the two sides of the rotor body 210 of the flat shape is less than the width of the base groove 112 in a direction perpendicular to the transverse opening of the bracket slot 112. The thickness of the rotor body 210 in a direction along the transverse opening of the bracket slot 211 (in long axis direction) is equal to the width of the base body 110 in short axis direction, and the thickness of the rotor body 210 in a direction along the transverse opening of the bracket slot 211 (in long axis direction) is less than the minimum width of the base groove 112. The minimum width is a width of the base groove 112 in a direction perpendicular to the transverse opening of the base groove 112 (a width of the bracket slot 211 in short axis direction when the rotor 20 being fitted in the base groove 112).

As shown in FIGS. 8 and 9, each of the first stopping groove 214 and the second stopping groove 215 includes an edge provided with inward flanging edges 216 of a curved surface, preferably, a smooth surface. The cover 220 comprises top edges corresponding to a groove wall of the first stopping groove 214 and a groove wall of the second stopping groove 215, configured to be concave to form sliding grooves matching the inward flanging edges 216, that is, in the vertical direction, two sides of the cover 220 in the direction perpendicular to the transverse opening of the bracket slot 211 form protuberances 221, i.e., sliding protuberance. The protuberances 221 match the inward flanging edges 216, and form a drawer-style open-close way with the flanging edges 216.

Figure 13:
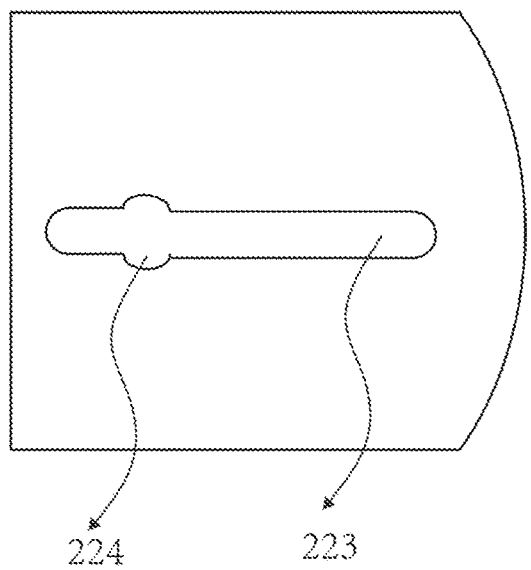
FIG. 13 is a bottom view illustrating a cover according to one embodiment of the present disclosure.
Figure 14:
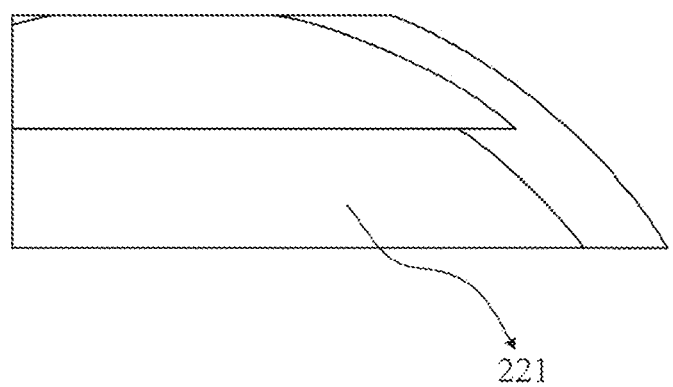
FIG. 14 is a front view illustrating a cover according to one embodiment of the present disclosure.
Figure 15:
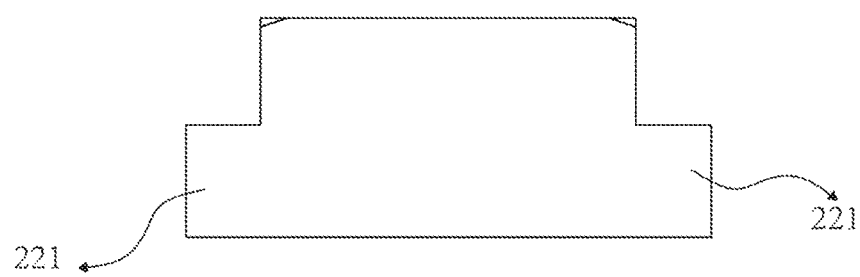
FIG. 15 is a left side view illustrating a cover according to one embodiment of the present disclosure.
Figure 16:
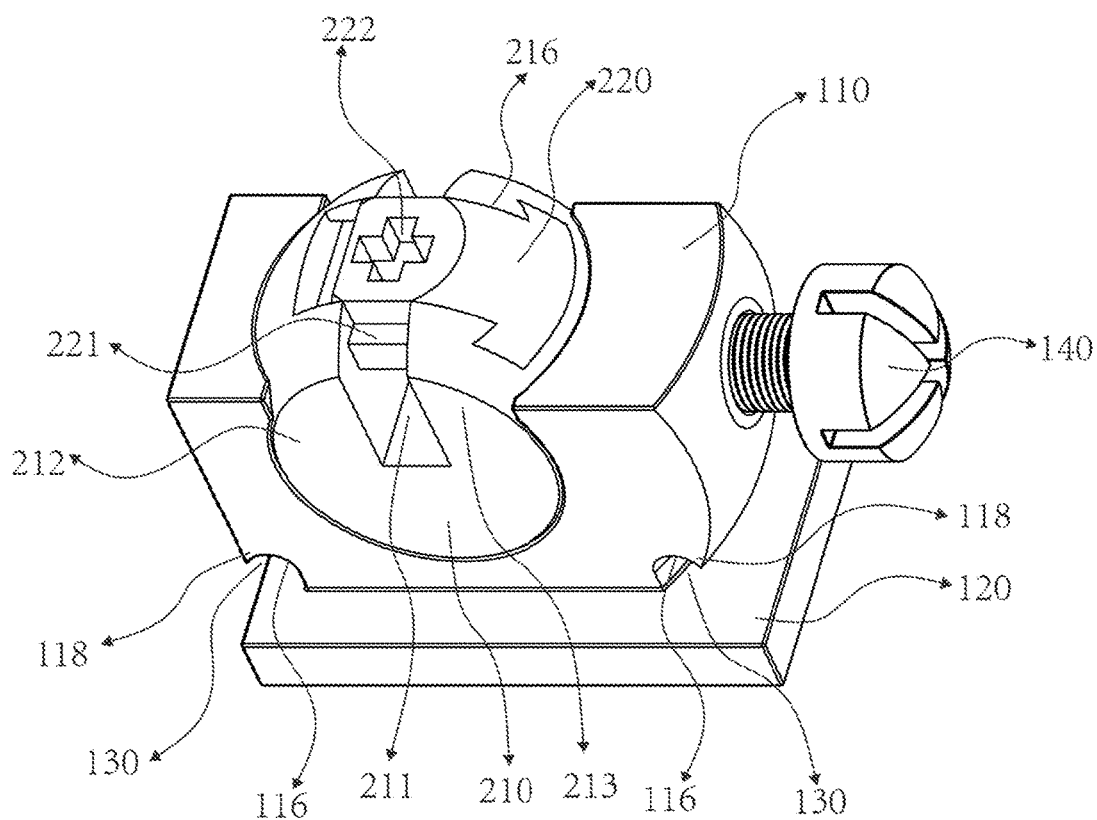
FIG. 16 is a plan view illustrating an adjustable bracket according to one embodiment of the present disclosure.
Figure 17:
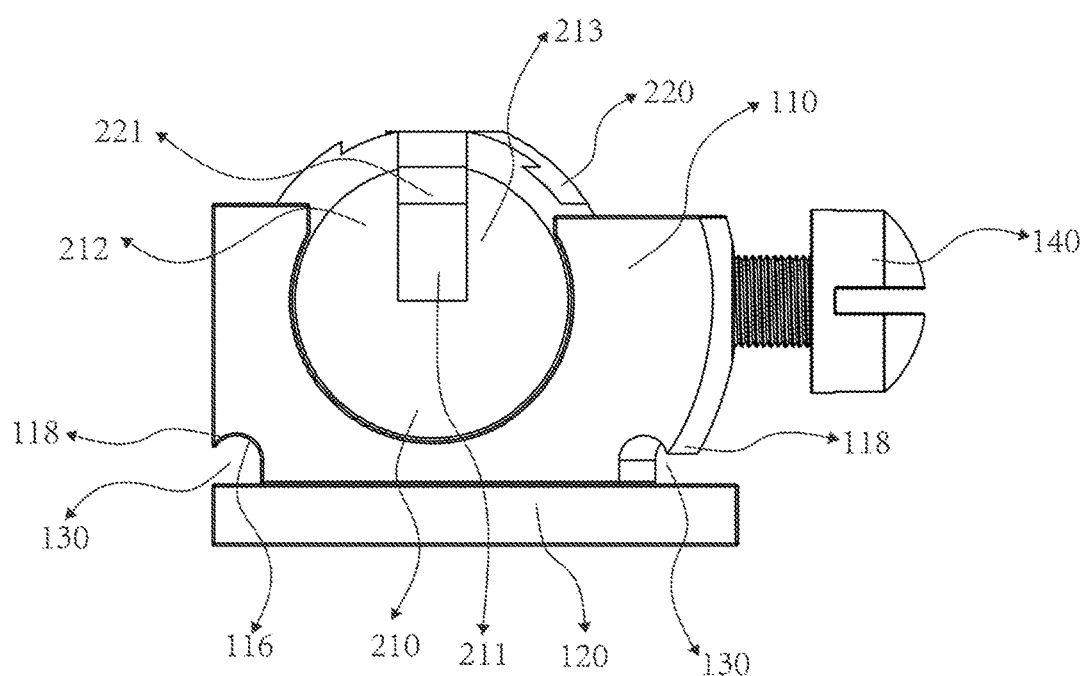
FIG. 17 is a front view illustrating an adjustable bracket according to one embodiment of the present disclosure.
Figure 18:
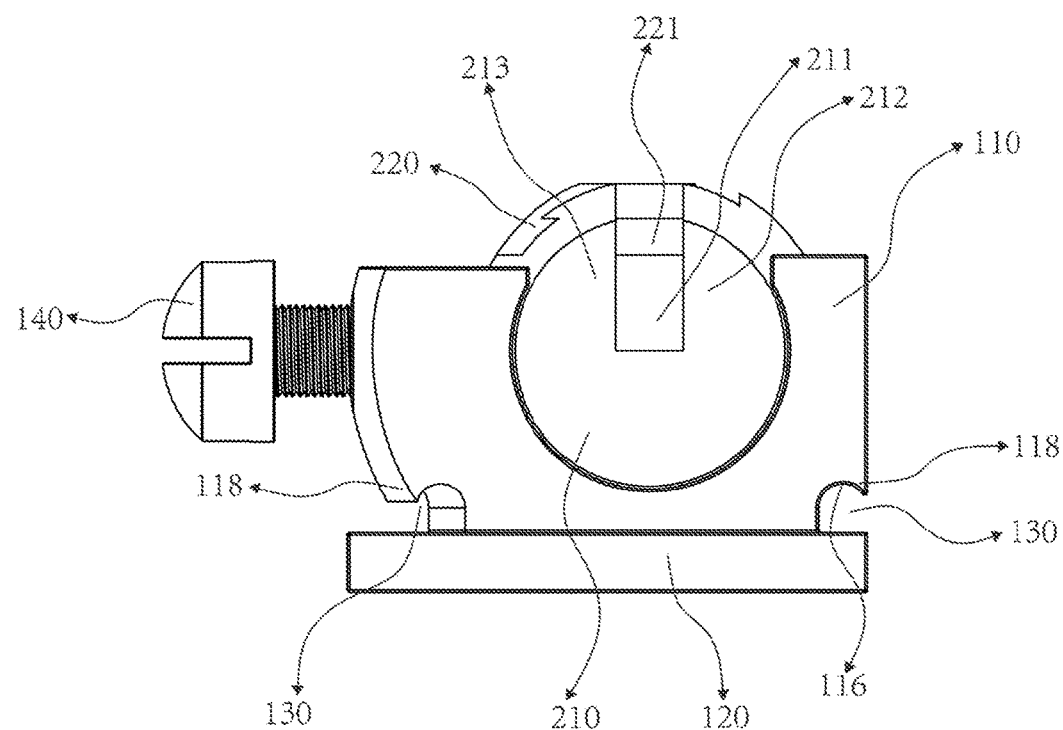
FIG. 18 is a back view illustrating an adjustable bracket according to one embodiment of the present disclosure.
Figure 19:
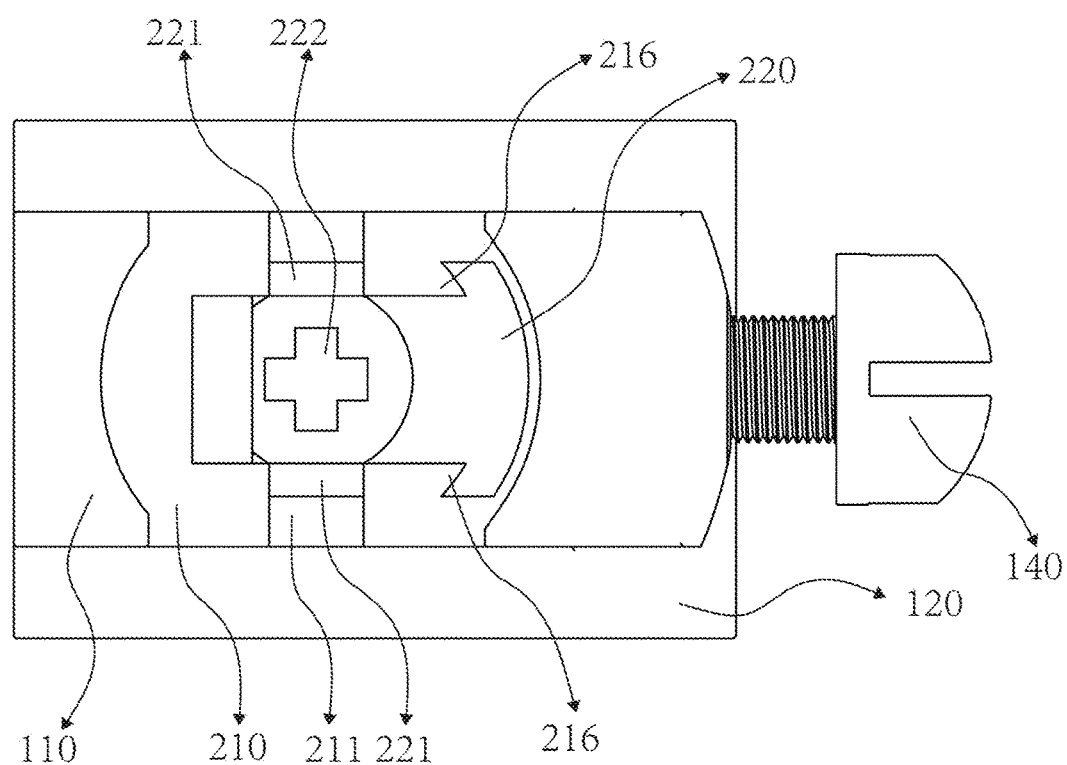
FIG. 19 is a top view illustrating an adjustable bracket according to one embodiment of the present disclosure.
Figure 20:
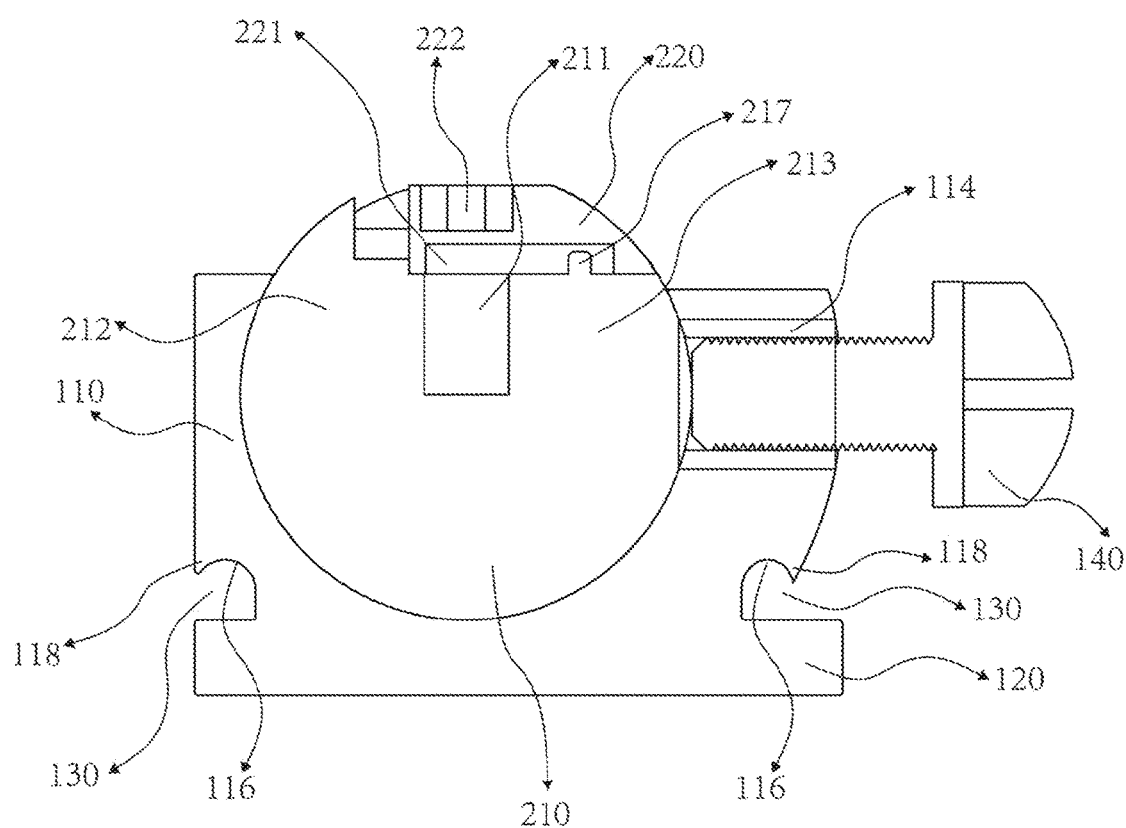
FIG. 20 is a section view illustrating an adjustable bracket according to one embodiment of the present disclosure.
Figure 21:
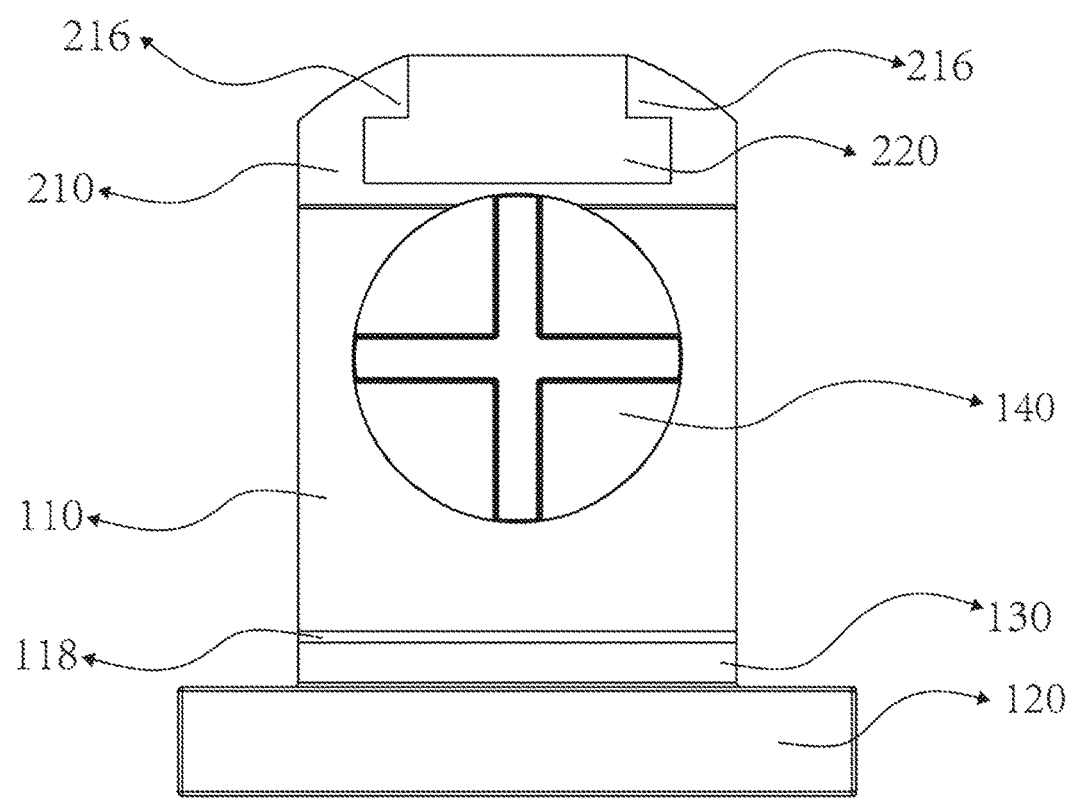
FIG. 21 is a right side view illustrating an adjustable bracket according to one embodiment of the present disclosure.
Figure 22:
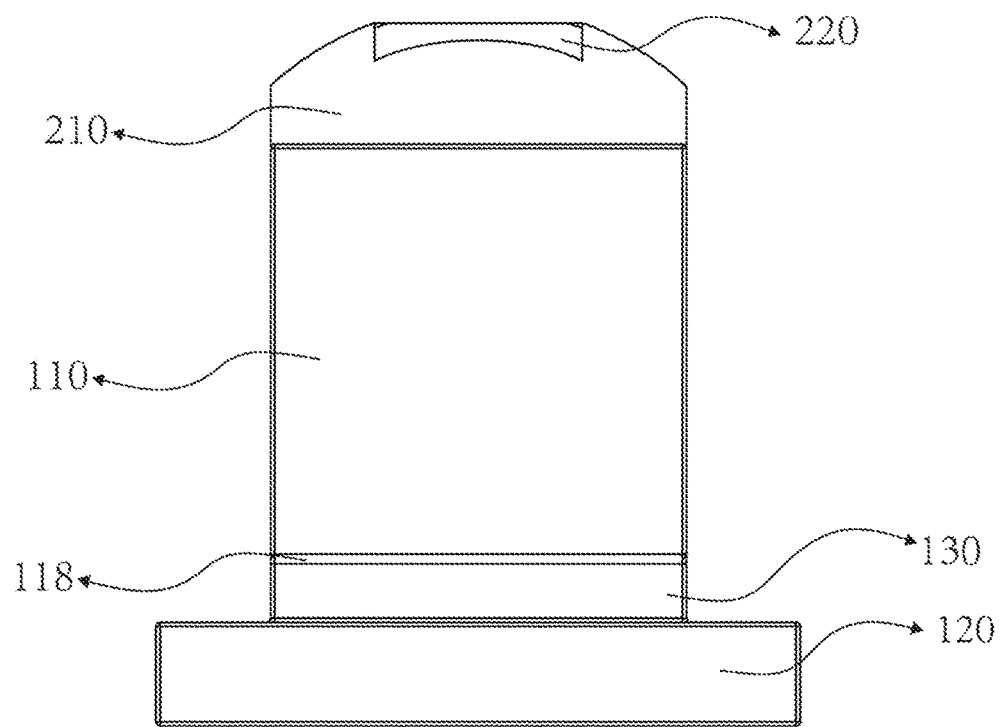
FIG. 22 is a left side view illustrating an adjustable bracket according to one embodiment of the present disclosure.
Figure 23:
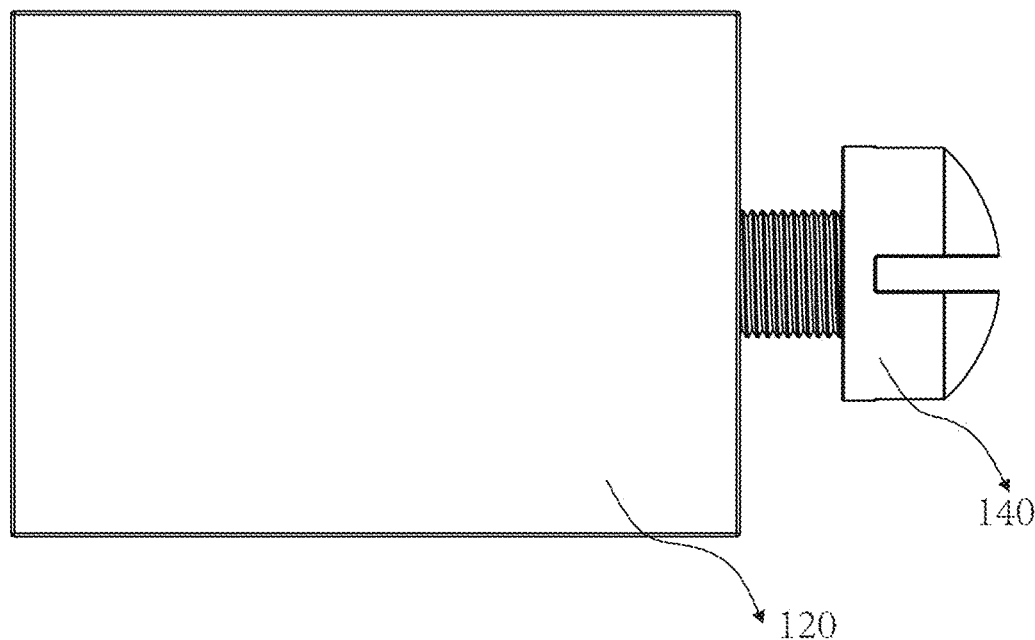
FIG. 23 is a bottom view illustrating an adjustable bracket according to one embodiment of the present disclosure.

As shown in FIGS. 8 and 9, the bottom of the second stopping groove 215 is provided with a sliding plug formed by the first bulge 217. As shown in FIG. 13, the bottom of the cover 220 is provided with a first groove 223 of an elongated shape. The first groove 223 has an opening. The long axis of the first groove 223 is perpendicular to a line joining two lateral openings of the base groove 112. The first groove 223 of the cover 220 is close to one side of the cover 220 facing the base groove 112. Further, the first bulge 217 has a larger size at the top of the first bulge 217 than at the bottom of the first bulge 217, the first groove 223 has a smaller size at the slot opening of the first groove 223 than at the inside of the first groove 223, and the slot opening of the first groove 223 is provided with a window 224 matching the top end of the first bulge 217 and adapted to be inserted by the top end of the first bulge 217. In the embodiment, the first bulge is an elastic component made of memory alloy, stainless steel, copper or any other appropriate elastic material. The role of the first bulge is to facilitate the closure between the cover 220 and the rotor body 210.

As shown in FIGS. 16-21, the base body 110 is provided with a positioning portion. In the embodiment, a thread through hole 114 passes through the base body 110 to form the positioning portion. One end of the thread through hole 114 is opened at the base groove 112, and the other end of the thread through hole 114 is opened at the surface of the main body 10. The thread through hole 114 is in a linear type and applied with a retaining screw 140 through which the rotor is fixedly connected to the main body. The screw cap of the retaining screw 140 is in a shape of cross, hexagon, pentagon or others general graphics. In the embodiment, the screw cap of the retaining screw 140 is in a shape of cross. An end of the retaining screw 140 towards the outside of the base body 110 protruding 0.2 to 8 mm from the surface of the base body 110, and the end of the retaining screw 140 is connected with a disc-shaped screw cap. The diameter of the screw cap is larger than that of the retaining screw 140. The portion of the retaining screw 140 protruding from the base body 110 can be used as a draw bolt. The adjustable brackets on surfaces of two interval or adjacent teeth can apply force on the two draw bolts by the stretch on the draw wire. During use, one of the adjustable brackets is fixed to the arch wire, and the other adjustable bracket on the surface of a tooth to be adjusted is not fixed to the arch wire. In this way, the adjustable bracket on the surface of a tooth to be adjusted can be drawn towards the other adjustable bracket by the effect of the draw wire, so that the tooth to be adjusted can be adjusted toward the required direction.

Further, as shown in FIGS. 16-18 and 20. The main body further includes a bottom plate 120. The bottom plate 120 may be in a shape of rectangle or other graphics. In the embodiment, the bottom plate 120 is in a shape of rectangle. The bottom plate 120 includes a top surface and a bottom surface. The base body 110 is fitted on the top surface of the bottom plate 120, one side of the edge of the base body 110 towards the top surface of the bottom plate 120 is provided with a recess 116, and the recess 116 and the bottom plate 120 form a second groove 130, i.e., ligation groove. In the embodiment, the adjustable bracket has four second grooves 130 (ligation grooves), and all second grooves 130 are distributed evenly on the side of the edge of the base body 110 towards the top surface of the bottom plate 120. The outer edge of the recess 116 is provided with a second bulge 118 which forms a protection wing to prevent the ligation wire from falling off. In addition, each side of the edge of the base body 110 towards the top surface of the bottom plate 120 may be provided with a recess 116, to form four recesses with elongated shapes. In the embodiment, two opposite sides of the edge of the base body 110 (at both ends of the long axis of the base body) are provided with a recess 116 respectively.

An orthodontics system with the bracket is also provided, including the adjustable bracket, arch wire, binder and accessories. The arch wire can pass through the bracket slot of the adjustable bracket. A plurality of adjustable brackets may be provided, and the number of the adjustable brackets may be from one to twenty, or above twenty, which can be determined by the number of the teeth to be corrected.

When the orthodontics system with the adjustable bracket is applied for orthodontic treatment, the orthodontic method includes the following steps.

In the embodiment, ten adjustable brackets are used to correct ten teeth, and each adjustable bracket has the same operation.

The rotor 20 of the orthodontics system is put in the base groove 112 of the main body 10, the rotor 20 can be movable within the base groove 112 to form the adjustable bracket, and the base body 110 of the adjustable bracket is fixed on the surface of a tooth by adhesion.

The cover 220 of the rotor 20 of each of the ten adjustable brackets is taken out, the arch wire of the orthodontics system passes through the bracket slots 211 of the ten adjustable brackets in turn, the rotors are enclosed by the respective covers 220, and the rotors 20 are turned respectively based on the location of the arch wire and the arrangement and form of the teeth, so that the bottom plate 110 of the main body 10 of each adjustable bracket can match the arrangement and form of each tooth respectively, the bracket slot 211 of the rotor 20 of each adjustable bracket can match the arrangement and form of the tooth respectively, and the channel inside the bracket slot 211 of each adjustable bracket can match the location of the arch wire. The arch wire may generate a deformation force, and the positioning portions of the base bodies 110 can position the rotors 20 respectively, that is, the rotor 20 can be positioned by the thread through hole 114 passing through the base body 110, and the retaining screw 140. A restoring force generated by the deformed arch wire is adapted to straighten the teeth.

Once the orthodontic treatment has been performed for a predetermined time period (It may be several weeks or months according to the condition of the teeth to be corrected), the positioning portion is reset (by unscrewing the retaining screw 140). The corresponding rotors 20 are turned again respectively according to the arrangement and form of a part of the corrected teeth of patient, and the corresponding rotors 20 are positioned again to allow the channel of the bracket slot 211 of each rotor 20 to match the position of the arch wire and angles of torque, tip and torsion presented in the bracket slot, and also allow the expression of the angles of torque, tip and torsion presented in the bracket slot of the rotator to be adaptable to a corresponding facial type defined by alveolar bone and skull, and the positioning portion on each base body 110 positions each rotor 20 respectively (by screwing the retaining screw 140). This process will be repeated until the teeth of the patient being corrected completely. A traditional orthodontic treatment generally needs to replace the arch wire 4 to 6 times during leveling and alignment stage, while resulting in no good effect with the influence of position where the bracket is being glued. The method of applying force has been changed in the present disclosure that the number of replacing the arch wire is reduced to 1 to 2 times while resulting in a better orthodontic effect.

In the orthodontics system with the bracket according to the present disclosure, the rotor 20 can be moved at any angle within the base groove 112 through the configuration of the adjustable bracket and the cooperating between the base groove 112 with a smooth curved surface provided in the main body 10 and the rotor 20 with a smooth curved surface of the adjustable bracket. After every adjustable bracket is fixed on the surface of the teeth through the respective base body 110, because the arrangement of the teeth may be irregular, and the arch wire for fixation may not completely match all the adjustable brackets, the rotor 10 can be moved at a certain angle following the line route of the arch wire so that the position of the bracket slot 211 can be adjusted to match the line route of the arch wire.

The orthodontics system with the bracket according to the present disclosure can be free to adjust the torque depending on the way for the orthodontic treatment and targets to be achieved by the orthodontic treatment. In addition, it is not required to replace the bracket for adjusting the torque of the bracket in the orthodontic treatment.

In addition, tip angle is an angle of inclination of the long axis of the tooth with the vertical centre line at a mesial direction and a distal direction, and may differ depending upon the race and the orthodontics system, as same as the torque angle of the bracket slot. The tip angle is adjustable that the angle of inclination of the tooth can be adjusted depending upon the doctor's experience. The inclination of the tooth is one of the most common dentofacial deformities, so the adjustable tip angle can slow down and reduce the force applied on the tooth to decrease the damage to the periodontium. Accurate adjustment can be also made for irregular teeth.

The turning angle of the tooth is adjustable. In the traditional brackets, there is no turning angle, so the dentist must glue the bracket on the center of tooth, but the tooth will be turned due to the crowding of teeth in many cases. Especially, the turning of the premolar is more common. Given this, the bracket may not be glued on the center of the tooth in many cases. However, for the bracket according to the present disclosure, the turning angle of the bracket is adjustable, so even if the bracket is not glued on the center of the tooth, the turning of the tooth can be corrected by adjusting the turning angle of the bracket.

The orthodontics system with the bracket according to the present disclosure can simplify the operation, and realize orthodontic treatment with light force through the configuration of the above adjustable bracket. It can be adjusted in various angles without the need to replace the bracket. For a severe displaced tooth, each slight angle adjustment can achieve a good orthodontic effect with a very light orthodontic force, and the force applied on the periodontium and the root is very slight, so the health of the periodontium and the root can be protected.

The orthodontic method of the adjustable bracket used in the orthodontics system with the bracket has advantages of convenient operation, simple producing, low cost, easy manual operation, saving time and manpower, and safe in use.

The above preferred embodiments of the present disclosure are described in detail, and should not be deemed as limitations to the scope of the present invention. It should be noted that variations and improvements will become apparent to those skilled in the art to which the present invention pertains without departing from its spirit and scope. Therefore, the scope of the present disclosure is defined by the appended claims.

The invention claimed is:

1. An adjustable bracket system, comprising:
   a main body, comprising a base body which is provided with a base groove; and
   a rotor, provided with a rotor body and a cover, wherein the top of the rotor body is provided with a bracket slot, the cover is adapted to cover the top of the rotor body and cover the top of a slot opening of the bracket slot, the rotor is adapted to be pivotably connected to the base body, the base body is further provided with a positioning portion for securing the rotor,
   wherein two sides of the rotor body respectively located at two ends of a transverse opening of the bracket slot are in a flat shape, the transverse opening having a length that extends between the two sides of the rotor body; and
   the thickness of the rotor body in a direction along the length of the transverse opening of the bracket slot is shorter than the minimum width of the base groove in a direction perpendicular to the length of the transverse opening of the bracket slot.

2. The adjustable bracket system according to claim 1, wherein the base groove has an inner wall shaped as a smooth curved surface; and
   the rotor has a smooth curved surface so that the rotor is in a shape similar to a sphere, and the rotor is disposed within the base groove and pivotably fit with the base groove.

3. The adjustable bracket system according to claim 2, wherein the base groove has an inner wall shaped as a smooth spherical surface; and
   the rotor body has a smooth spherical surface, and the cover has a spherical surface that matches the surface of the rotor body.

4. The adjusting bracket system according to claim 1, wherein the surfaces of two sides of the base body respectively located at two ends of a transverse opening of the base groove are in flat shape.

5. The adjustable bracket system according to claim 1, wherein the main body further comprises a bottom plate comprising a top surface and a bottom surface, the base body is fitted on the top surface of the bottom plate, one side of the edge of the base body towards the top surface of the bottom plate is provided with a recess, and the recess and the bottom plate form a second groove; and
   at least two second grooves are formed, and all second grooves are distributed evenly on the side of the edge of the base body towards the top surface of the bottom plate.

6. The adjustable bracket system according to claim 1, wherein a guide groove is arranged on the top of the cover.

7. The adjustable bracket system according to claim 1, wherein the base body is provided with a thread through hole to form the positioning portion, one end of the thread through hole is opened at the inner wall of the base groove, the other end of the thread through hole is opened at the surface of the main body, and the thread through hole is fitted with a retaining screw through which the rotor is fixedly connected to the main body.

8. The adjustable bracket system according to claim 7, wherein an end of the retaining screw towards the outside of the base body is protruding 0.2 to 8 mm from the surface of the base body, and the end of the retaining screw is connected with a screw cap which protrudes radially and outwardly from the outer wall of the retaining screw.

9. An adjustable bracket system, comprising:
a main body, comprising a base body which is provided with a base groove; and
a rotor, provided with a rotor body and a cover, wherein the top of the rotor body is provided with a bracket slot, the cover is adapted to cover the top of the rotor body and cover the top of a slot opening of the bracket slot, the rotor is adapted to be pivotably connected to the base body, the base body is further provided with a positioning portion for securing the rotor,
wherein the bracket slot divides the rotor body into a first end portion and a second end portion, a first stopping groove is provided at the top of the first end portion, and the first stopping groove is provided with a stopping opening located in the bracket slot,
wherein a second stopping groove is provided at the top of the second end portion, and the second stopping groove is provided with two sliding openings located in the same axis as the stopping opening of first stopping groove,
wherein the cover is adapted to be held in the first and second stopping grooves, and cover the top of the slot opening of the bracket slot,
wherein the bottom of the second stopping groove is provided with a first bulge, the bottom of the cover is provided with a first groove with an elongated shape, and the long axis of the first groove is perpendicular to a line route joining two lateral openings of the base groove, and
wherein the first groove has a smaller size at the slot opening of the first groove than at the inside of the first groove, and the slot opening of the first groove is provided with a window matching the top end of the first bulge and adapted to be inserted by the top end of the first bulge.

10. The adjustable bracket system according to claim 9, wherein each of the first stopping groove and the second stopping groove comprises inward flanging edges with a round smooth shape; and
the cover comprises top edges corresponding to a groove wall of the first stopping groove and a groove wall of the second stopping groove, configured to be concave to form sliding grooves matching the inward flanging edges.

11. The adjustable bracket system according to claim 9, wherein the first bulge is an elastic component.

12. An orthodontics system, comprising an arch wire, and further comprising the adjustable bracket system according to claim 1, wherein the arch wire passes through the bracket slot of the adjustable bracket.

13. An orthodontic method of using the orthodontics system of claim 12, comprising:
fixing the base body of the main body of the adjustable bracket on the surface of a tooth by adhesion;
passing the arch wire through the bracket slot of the adjustable bracket, covering the rotor with the cover, fixing the arch wire, and turning the rotor to allow a bottom plate of the main body of the adjustable bracket to match the arrangement and form of teeth, also allow the bracket slot of the rotor of the adjustable bracket to adapt the arrangement and form of the teeth, and further allow a channel of the bracket slot of the rotor of the adjustable bracket to adapt the position of the arch wire, wherein the arch wire generates a deformation force, the positioning portion of the base body positions the rotor, and a restoring force generated by the deformated arch wire is adapted to correct the teeth; and
resetting the positioning portion once the orthodontic treatment has been performed for a predetermined time period, turning the corresponding rotor respectively again according to the arrangement and form of a part of the corrected teeth of the patient, correcting and positioning the corresponding rotor to allow the channel of the bracket slot of the rotor to match the position of the arch wire, and also allow the expression of the angles of torque, tip and torsion presented in the bracket slot of the rotator to be adaptable to a corresponding facial type defined by alveolar bone and skull, and repeating the resetting, turning, correcting and positioning process to let the positioning portion on the base body position the rotor.

* * * * *